United States Patent
Gamberini

[11] Patent Number: 5,275,308
[45] Date of Patent: Jan. 4, 1994

[54] DISPENSING MACHINE FOR POWDER-BASED PRODUCTS WITH AN IMPROVED DEVICE FOR LEVELLING AND HOMOGENIZATION OF SUCH PRODUCTS

[75] Inventor: Ernesto Gamberini, Rostignano-Pianoro, Italy

[73] Assignee: MG2 S.p.A., Pianoro, Italy

[21] Appl. No.: 856,253

[22] Filed: Mar. 25, 1992

[30] Foreign Application Priority Data

Mar. 26, 1991 [IT] Italy ............. B091A 000093

[51] Int. Cl.$^5$ ............................................. B67D 5/00
[52] U.S. Cl. ...................................... 222/64; 222/80; 222/162; 222/168; 222/190; 222/217
[58] Field of Search ............... 222/52, 64, 80, 162, 222/163, 167, 168, 190, 216, 217, 224

[56] References Cited

U.S. PATENT DOCUMENTS

| | | | |
|---|---|---|---|
| 1,453,143 | 4/1923 | Johnson et al. | 222/167 X |
| 3,414,164 | 12/1968 | McKay | 222/64 |
| 3,501,894 | 3/1970 | Hayashi et al. | 53/28 |
| 3,951,309 | 4/1976 | Kadowaki | 222/64 |
| 4,171,071 | 10/1979 | Cumpston | 222/167 |
| 4,560,092 | 12/1985 | Souza | 222/168 |
| 4,574,984 | 3/1986 | Bonerb | 222/64 X |

FOREIGN PATENT DOCUMENTS

| | | |
|---|---|---|
| WO8911462 | 11/1989 | PCT Int'l Appl. |
| 2195983 | 4/1988 | United Kingdom. |
| 2238768 | 6/1991 | United Kingdom. |

Primary Examiner—Andres Kashnikow
Assistant Examiner—J. A. Kaufman
Attorney, Agent, or Firm—Ladas & Parry

[57] ABSTRACT

A machine for dispensing powder products into suitable receptacles comprises a rotating container in which is defined a withdrawal zone, a dispensing unit, and a fixed device which levels the produce in the container. The device includes a member located upstream of the withdrawal zone and having a first portion which levels the product into a layer and a second portion which defines a channel which directs the product accumulated on this first portion in excess of the layer, towards a part of the container downstream of the withdrawal zone; and a member positioned downstream of the withdrawal zone, along which the excess product slides. The latter member defines with a central part of the container, a passage which directs the excess product towards a part of the container upstream of the fixed device.

23 Claims, 4 Drawing Sheets

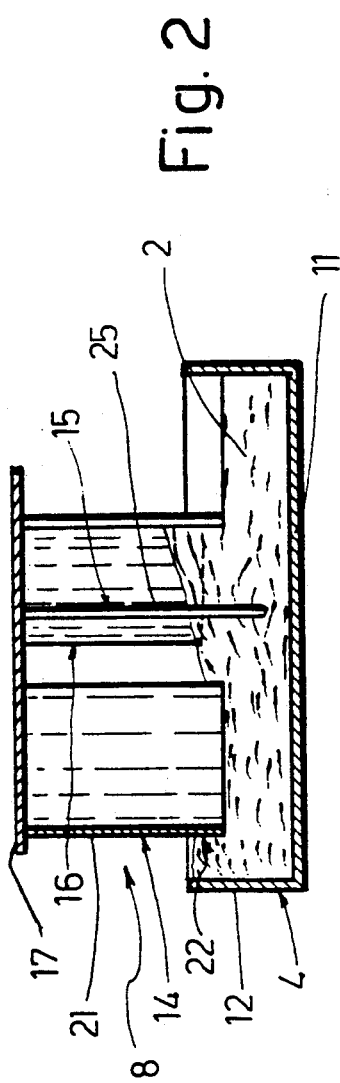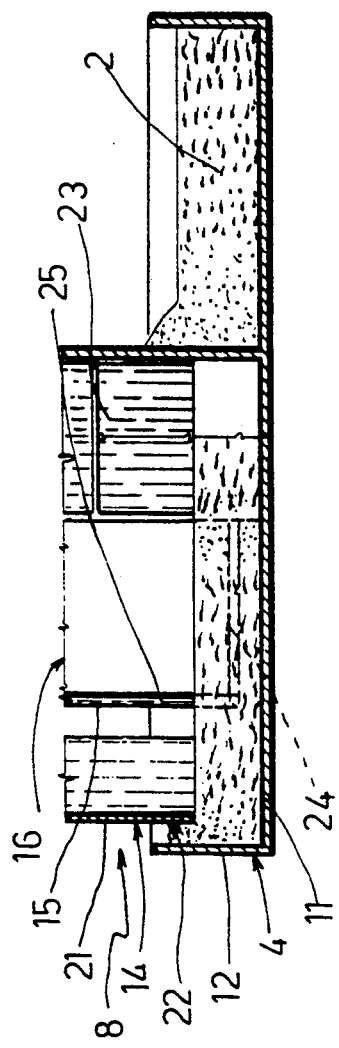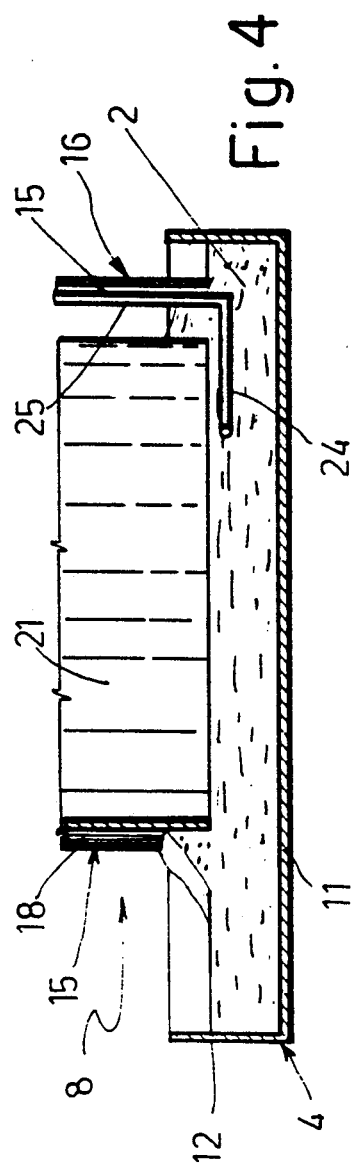

DISPENSING MACHINE FOR POWDER-BASED PRODUCTS WITH AN IMPROVED DEVICE FOR LEVELLING AND HOMOGENIZATION OF SUCH PRODUCTS

BACKGROUND OF THE INVENTION

The present invention relates to a machine for dispensing powder-based products with an improved device for levelling and homogenization of such products.

As is known, devices of the above indicated type installed in dispensing machines comprise a fixed wall and a bar, also fixed, installed within a rotating container respectively upstream and downstream of the region in which the product is withdrawn by the dispensers. The lower edge of this wall is at a predetermined distance from the bottom wall of the container so that this fixed wall causes levelling of the layer of products. The bar, on the other-hand, performs the function of mixing the product to re-cover the recesses left in the layer by the dispensers.

The above-described devices have several disadvantages which cause an insufficient precision in the quantity of product dispensed from the container, and which is then distributed into doses. In fact, current devices do not sufficiently insure the re-covering of the recesses left by the dispensers and the continuous and constant circulation of the product. These disadvantages are due primarily to the fact that the fixed wall, which is normally in a radial position with respect to the center of rotation of the container, causes an accumulation of the product which cannot pass between this fixed wall and the bottom wall of the container. The product accumulated on the fixed wall is often stationary for a long time, so that it is possible that it or part of it deteriorates due to the presence of oxygen and/or due to being hygroscopic, with the consequent formation of a single large lump or several lumps. It is evident that the presence of lumps reduces the effectiveness of the levelling and homogenization.

SUMMARY OF THE INVENTION

The object of the present invention is to provide a dispensing machine including a device for levelling and homogenization of the power-based products which will be free from the stated disadvantages.

According to the present invention there is provided a dispensing machine for powder-based products, of the type comprising a container in which a product withdrawal zone is defined, a dispensing unit operable to withdraw the said product from the said zone and to deposit it into appropriate receptacles, a first levelling and homogenization device for the said product in the said container, and means for relatively rotating the said container and the said first device, characterized by the fact that the said first device comprises:

a first member installed upstream of the said zone, the lower edge of which lies at a predetermined and constant distance from a bottom wall of the said container, and has a first portion which causes levelling of the said product at a predetermined height, and a second portion which extends from the first and defines, together with a part of a side wall of the said container, a channel which aids the flow of the said product in excess of the said layer of predetermined height, which accumulates on the said first portion, directing it towards a part of the said container downstream of the said zone;

a second member installed downstream of the said zone and operable to cause, after withdrawal of the product, homogenization of the said product in the said layer and the said product directed along the said channel; and a third member installed downstream of the said second member, the lower edge of which is substantially at the same level as the corresponding edge of the said first member with respect to the said bottom wall, having a face along which the said excess product slides, and defining with a central part of the said container a passage which allows the said excess product to flow towards a part of the said container upstream of the said first member.

BRIEF DESCRIPTION OF THE DRAWINGS

For a better understanding of the present invention two preferred embodiments will now be described, purely by way of non-limitative example, with reference to the attached drawings, in which:

FIGS. 2, 3 and 4 are sections taken on lines II—II, III—III and IV—IV respectively in FIG. 1;

DETAILED DESCRIPTION OF THE INVENTION

Figure 1:
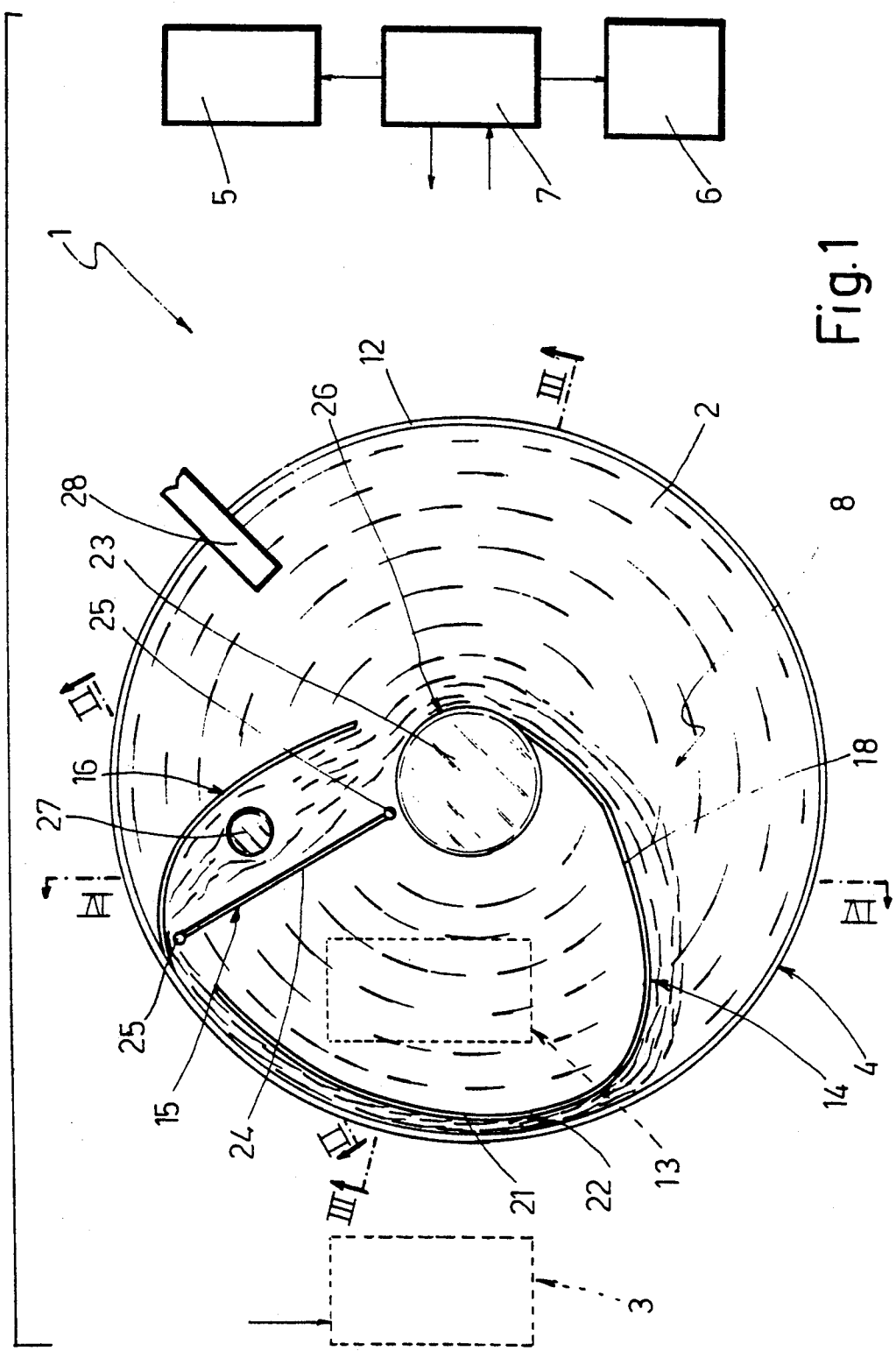
FIG. 1 is a partial plan view of a first embodiment of dispensing machine provided with a powder product levelling and homogenization device.

As illustrated in FIG. 1 the reference numeral 1 generally indicates a dispensing machine for any type of powder product 2 and, for example, of pharmaceutical, food or cosmetic type. The machine 1 essentially comprises a dispensing unit 3 (illustrated in broken outline), a rotating container 4, a device 5 for feeding product 2 into the container 4, an electric motor 6 for driving the container 4, a central electronic processing or control unit 7 for management and control of the unit 3, the device 5 and the motor 6, and a device 8 for levelling and homogenization of the product 2 within the container 4.

In use the central control unit 7 controls the unit 3 to cause this to withdraw product 2 from container 4 and to divide the product 2 thus withdrawn into receptacles defined for example in capsules, blister pack recesses, small glass or other material receptacles etc. Apart from the device 8 all the components of the machine 1 are of known type and for this reason illustrated only schematically.

The container 4 has a horizontal bottom wall 11 and a cylindrical side wall 12. As already indicated the container 4 is rotatable and in particular turns in a clockwise direction as viewed in FIG. 1. Within the container 4 it is possible to define a zone 13 (illustrated in broken outline) from which the unit 3 withdraws the product 2 and for this purpose requires that the product be in the form of a levelled and constant layer. To form this levelled and constant layer the quantity of product 2 present in the container 4 must be greater than that represented by this layer defined over the whole of the container 4. For this a part of the product 2 in excess of the said layer is held stationary before the zone 13. The device 8 is shaped in such a way as to define the said layer and to cause the product 2 in excess of this layer to be recirculated.

With reference to FIGS. 1 to 4, the device 8 comprises:

a first fixed member 14 installed upstream of the zone 13, which causes levelling of the product 2 into a layer of predetermined height, and which aids the flow of product 2 which accumulates on it towards a region downstream of the zone 13;

a second fixed member 15 installed downstream of the zone 13 and operable to cause homogenization of the product 2 in the predetermined layer after the product withdrawal; and a third fixed member 16 installed downstream of the member 15 and operable to receive the flow of product 2 from the member 14 and to direct this flow towards a region of the container 4 upstream of the member 14.

The references to upstream and downstream are made in relation to the direction of rotation of the container 4. The members 14, 15 and 16 are supported from above (FIG. 2) by a common fixed plate 17 parallel to the wall 11. It is clear that, in dependence on the thickness of the layer to be formed in the zone 13, the machine 1 can provide for adjustment of the level of the plate 17.

The member 14 comprises a vertical wall the lower edge of which lies at a predetermined and constant distance from the bottom wall 11. The wall formed by the member 14 has a first portion 18 which extends longitudinally in a parabolic curve concave towards the zone 13 and a second portion 21 which extends from the first and which defines, with a part of the wall 12, a channel 22. The channel 22 has an exit opening which is close to the wall 12, downstream of the zone 13 and immediately upstream of the members 15 and 16. The portion 18 extends from a central boss 23 of the container 4 tangentially of this boss 23 and terminates close to the wall 12 by which it defines the entrance opening of the channel 22. In order to define the channel 22 the portion 21 extends longitudinally almost parallel to the corresponding part of the wall 12. In reality, from the said inlet opening, the channel 22 has a uniformly increasing width as illustrated in FIG. 1. Naturally, the product 2 which gradually accumulates on the convex face of the portion 18 flows along the channel 22. The product 2 which is below the lower edge of the first member 14 continues to follow the container 4 or rather remains in the same position with respect to the corresponding underlying zone of the wall 11. The zone 13 is defined between the face of the portion 21 outside the channel 22 and the central boss 23.

The member 15 is an ordinary homogenizer defined by a horizontal rectilinear bar 24 having a longitudinal axis which is radial with respect to the central boss 23 and two vertical arms 25 fixed to the plate 17. The bar 24 lies at a lower level than that of the lower edge of the member 14 so that it lies in the layer of product 2 defined in the zone 13. The bar 24 has a first end close to the central boss 23 and a second end close to the wall 12 and, in particular, immediately downstream of the outlet opening of the channel 22. The layer of product 2 which leaves the zone 13 has recesses in it left by the dispensers of the unit 3. When this layer meets the member 15 this causes a mixing of the product 2 which causes the recess to disappear and which homogenizes the product 2 in such a way as to pulverize possible lumps which may be formed as a result of the pressure on the product 2 exerted by the dispensers.

With reference to FIGS. 1 to 4, the member 16 is defined by a vertical wall which extends longitudinally along a parabolic curve which is concave towards the zone 13. In particular, the wall which constitutes the member 16 extends close to the side wall 12 immediately downstream of the outlet opening of the channel 22 and terminates close to the central boss 23 defining therewith a passage 26. The side of the member 16 close to the wall 12 brushes this in such a way as to prevent passage of product 2 other than through the passage 26. The lower edge of the member 16 lies at a predetermined constant distance from the bottom wall 11, which distance is equal to that defined between the member 14 and the bottom wall 11.

With reference to FIG. 1 a level sensor 27 is installed between the members 15 and 16. The sensor 27 detects the level of the product 2 which accumulates on the member 16 in excess of the predetermined layer and informs the central control unit 7. If a level below a predetermined level is detected the central control unit controls the device 5 which in turn introduces a predetermined quantity of product 2 into the container 4 upstream of the member 14 via an outlet opening 28 of a hopper (not illustrated).

In use, during rotation of the container 4, the device 8 levels the product 2 into a layer of a thickness equal to the predetermined distance between the members 14 and 16 and the wall 11. The product in excess of this layer gradually accumulates on the convex face of the portion 18 and from here, by rotation of the container 4 and due to the shape of the member 14, creates a constant flow of excess product 2 which is channelled along the channel 22 outside the zone 13 and towards the concave face of the member 16 Due to rotation of the container 4 and the shape of the member 16 the excess product accumulated on the concave face of the member 16 is channelled, after having traversed the passage 26, towards the convex face of the portion 18. During the above described flow it will appear evident that the excess product 2 is mixed with the product 2 defined in the underlying layer. This remixing is also encouraged by the member 15 which is located along the direction of flow defined between the outlet opening of the channel 22 and the concave face of the member 16. Because of all this it is improbable that the excess product 2 will remain for long periods above the underlying layer.

Figure 5:
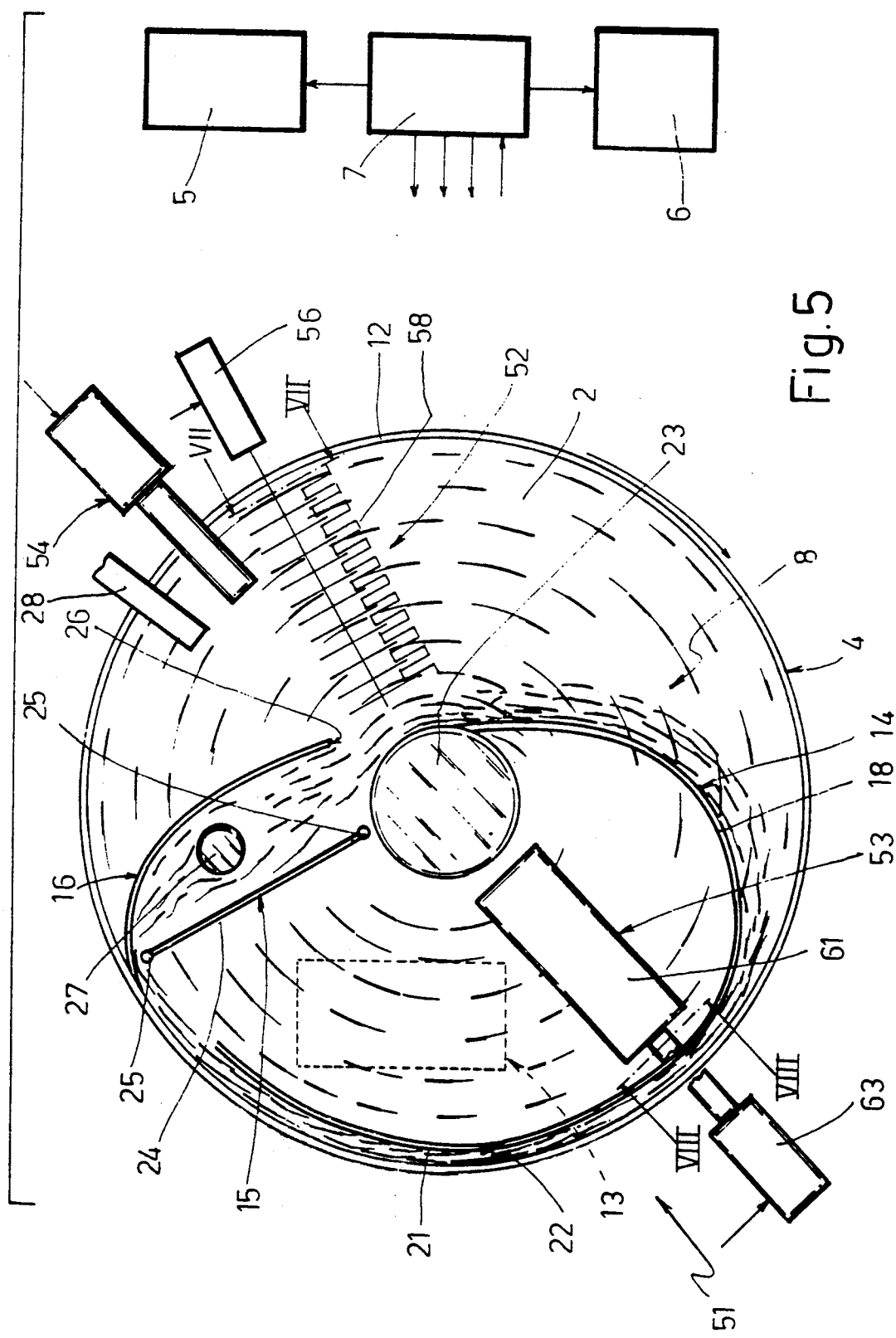
FIG. 5 is a partial plan view of a second embodiment of a dispensing machine provided with a device for levelling and homogenization of powder-based products having a certain degree of moisture absorbency.

In FIG. 5 there is illustrated, and indicated by the reference numeral 51, a machine similar to the machine 1 but intended for use with powder-based products having a predetermined hygroscopic property. The machine 51 has the same characteristics as the machine for which reason its components will be indicated with the same reference numerals as the machine 1. It is known that in rotating containers the granules of products of the above-indicated type tend to aggregate so as to define pellets of different diameters. The differences between the machines 1 and 51 are all due to the fact that in the machine 51 it is necessary to work with pellets and not just with powder.

The machine 51 is provided with three devices 52, 53 and 54 operated by the central control unit 7 and of which the device 52 is installed upstream of the member 14 and is operable to provide pellets of substantially equal diameter, the device 53 is installed between the portion 18 and the zone 13 and is operable to compress the pellets slightly in such a way as to give the pellets a substantially ovoid form, and the device 54 is installed downstream of the member 16 and is operable to supply to the container 4 predetermined quantities of additives which determine the hygroscopicity of the product 2. In this case, therefore, the product, in powder form, is supplied by means of the device 5 and the additive which causes the powder to be hygroscopic is supplied by means of the device 54. It will be evident that in a different arrangement the container 4 could be supplied with a product 2 having the additive already in it. To assist the installation of the device 53, the portion 18 is further upstream of the zone 13 then the corresponding component illustrated in FIG. 1. For this reason the portion 21 and therefore the channel 22 have a greater longitudinal extent than those of the machine 1.

Figure 6:
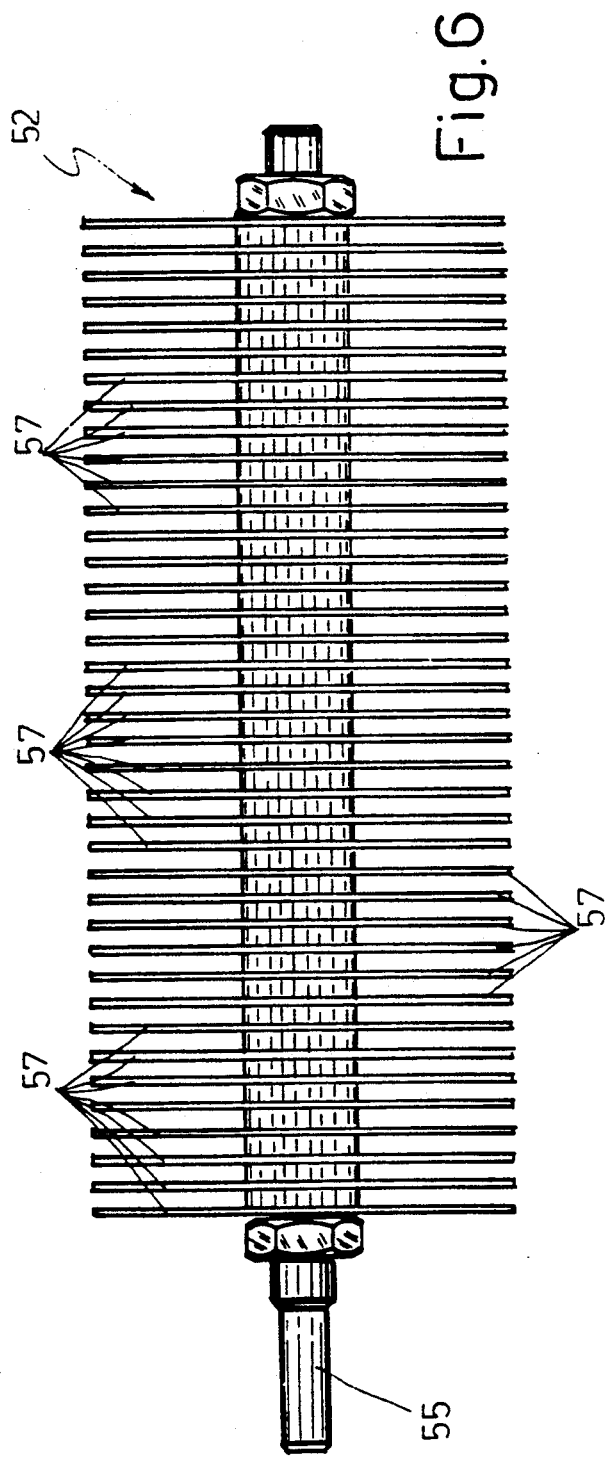
FIG. 6 is a view of one member of the device of FIG. 5.
Figure 7:
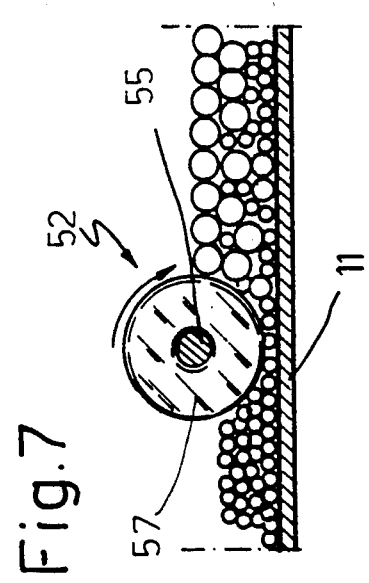
FIG. 7 is a sectional view taken on the line VII—VII in FIG. 5.

With reference to FIGS. 5, 6 and 7, the device 52 has a rotatable, horizontal shaft 55 driven by an electric motor 56 controlled by the central control unit 7 and a plurality of disc knives 57 fitted centrally on the shaft 55. In particular the knives 57 are uniformly distributed along the longitudinal axis of the shaft 55. The distance between adjacent knives 57 determines the diameter of the pellets. The first knife 57 of the device 52 is close to the wall 12 and the last knife 57 is close to the passage 26. Preferably the axis of the shaft 55 extends radially of the container 4. The lower edge of the knives 57 lie at a short distance from the bottom wall (FIG. 7) and in particular at a distance substantially close to the distance between two adjacent knives 57. The device 52 further includes a fixed scraper member 58 schematically illustrated in FIG. 5 and operable to free the blades 57 from possible pellets or lumps which adhere thereto. The shaft 55 rotates in a clockwise direction when viewed as seen in FIG. 7 with a speed which depends on the type of product 2 and the dimensional characteristics which it is desired to obtain in the pellets leaving the device 52.

In use of the machine the pellets which arrive at the device 52 have different diameters, normally greater than the distance between two adjacent blades 57. During the traverse through their space defined between the blades 57 these pellets are reduced in diameter to that equal to the distance between adjacent blades 57 so that, as they leave the device 52 and therefore as they approach the member 14 all the pellets have a substantially equal diameter. The member 14 acts both to form a level and constant layer of such pellets and also serves the function of causing the excess pellets above this layer to flow towards the member 16 as already described for the machine 1.

Figure 8:
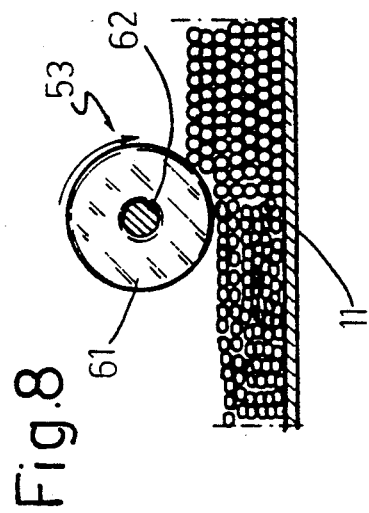
FIG. 8 is a sectional view taken on the line VIII—VIII of FIG. 5.

As illustrated in FIGS. 5 and 8, the device 53 is a pellet compactor device which compacts the pellets which form the said layer. It performs a minimum compaction to assist the withdrawal of the pellets by the dispensers, in that by experimentation it has been found that the ovoid or squashed spherical form inhibits the pellets withdrawn by the dispensers from falling during movement of these towards the distribution stage. The device 53 includes a cylindrical roller 61 fitted on a horizontal rotatable shaft 62 which is driven by an electric motor 63 controlled by the central control unit 7. The longitudinal axis of the roller 61 preferably extends radially of the container 4.

The roller 61 has a length slightly less than the distance between the central boss 23 and the wall 12 and decidedly greater than the width of the zone 13 which as already indicated is immediately downstream thereof. The distance between the roller 61 and the wall 11 is slightly less than that defined between the member 14 and the bottom wall 11. The shaft 62 rotates in a clockwise direction as seen in FIG. 8 with a speed which depends upon the type of product 2 and the dimensional characteristics which it is desired to obtain in the pellets leaving the device 53. The considerations concerning the flow of excess product 2 described in relation to the machine 1 also apply to the machine 51.

From what has been described above the advantages achieved with the embodiments of the present invention will be apparent.

In particular, in the machines 1 and 51 a high precision in the quantity of product which each dispenser withdraws from the container is achieved in that the device 8 ensures both the complete re-covering of the depressions left by the dispensers and the continuous and constant circulation of the product. In fact, the device 8, as hereinabove described, channels the excess product, that is to say the product which does not pass between the member 14 and the bottom wall of the container 4, towards a region downstream of the withdrawal zone 13, in which the excess product is mixed with the underlying layer. The product which accumulates on the convex face of the portion 18 remains on this for a limited time and therefore is not subject to possible deterioration. For product which is only in powder form the absorbtion of moisture and therefore the formation of lumps is less probable. For powder-based product having a predetermined degree of moisture and for which the formation of lumps is inevitable the device 52 makes the diameter of such lumps uniform and the device 53 compacts these lumps to assist the withdrawal thereof.

Finally, it is clear that the machines 1 and 51 described and illustrated here can have modifications and variations introduced thereto without departing from the scope of the present invention.

In particular in the machine 51 the device 52 need not be driven and, for example, the shaft 55 could be fixed and the blades 57 mounted freely rotatably thereon, or else the blades 57 could be fixed to the shaft 55 and this mounted freely rotatably between two lateral supports. Similarly the device 53 need not be driven and, for example, the roller 61 could be mounted freely rotatably on the shaft 62 which in this case is fixed, or the roller 61 could be fixed to the shaft 62 which in this case could be mounted freely rotatably between two lateral supports. Both for the machine 1 and for the machine 51 relative movement is necessary between the device 8 and the container 4, for which it is possible to arrange for the device 8 to be rotating and the container 4 fixed. Naturally in this case, in the machine 51 the device 8 must also drive the devices 52 and 53 to rotate. The withdrawal of the product 2 can be achieved in a different way and, for example, in machines of alternating type a dispensing unit may be provided which, in succession, translates horizontally towards the container 4, then translates into the layer for the withdrawal phase, and finally returns into the original position where it dispenses the product into appropriate receptacles. In continuously operating machines the withdrawal could be achieved by at least one dispenser which rotates with the same speed as the container and which performs a withdrawal stage in the zone 13 and a dispensing stage into a suitable receptacle at a different region of the machine.

What is claimed is:

1. A machine for dispensing powder-based products (2) of the type comprising a container (4) in which is defined a product withdrawal zone (13), a dispensing unit (3) adapted to withdraw the said product (2) from the said zone (13) and deposit it into suitable receptacles, a first device (8) for levelling and homogenization of the said product (2) in the said container (4), and means (6) for relative rotation between the said container (4) and the said first device (8), said first device (8) comprising:

a first member (14) installed upstream of the said zone (13), said first member having a lower edge which lies at a predetermined and constant distance from a bottom wall (11) of the said container (4), and further having a first portion (18) which causes levelling of the said product (2) into a layer of predetermined thickness and a second portion (21) which extends from the first portion and which defines, with a part of a side wall (12) of the said container (4), a channel (22) which directs flow of the said product (2) which accumulates on the said first portion (18) in excess of the said layer, towards a part of the said container (4) downstream of the said zone (13);

a second member (15) installed downstream of the said zone (13) and operable to cause, after withdrawal of the product, homogenization of the said product (2) in the said layer and the said product (2) channelled by the said channel (22); and a third member (16) installed downstream of the said second member (15), said third member having a lower edge which lies substantially at the same level as the lower edge of the said first member (14) with respect to the said bottom wall (11), said third member further having a face along which the said product (2) in excess of the said layer slides, and defining, with a central part (23) of the said container (4), a passage (26) which allows the said product (2) in excess of the said layer to flow towards a part of the container (4) upstream of the said first member (14).

2. A machine according to claim 1, which further comprises:

a level sensor (27) installed between the said second member (15) and the said third member (16) and operable to detect the level of the said product (2) in excess of the said layer;

a second feed device (5) for supplying the said product (2) to the said container (4); and an electronic central control unit (7) to which the said sensor (27) is connected, and operable to control the said means (6) which provides the relative rotation between the container and the said first device (8) and the said second feed device (5) when the level of the said product (2) in excess of the said layer falls below a predetermined value.

3. A machine according to claim 2, wherein said lateral wall (12) of the said container (4) is cylindrical.

4. A machine according to claim 3, wherein said first portion (18) extends longitudinally along a parabolic curve which is concave towards the said zone (13) and extends from the said central part (23) of the said container (4) tangentially of the said central part (23) and terminates close to the said side wall (12) with which it defines an inlet opening of the said channel (22); said channel having an outlet opening which is close to the said side wall (12) downstream of the zone (13) and immediately upstream of the said second and third members (15) and (16).

5. A machine according to claim 4, wherein said second portion (21) extends longitudinally substantially parallel to the said side wall (12).

6. A machine according to claim 5, wherein said channel (22) has a width increasing, in a uniform manner, from the said inlet opening to the said outlet opening.

7. A machine according to claim 1,
wherein said second member (15) comprises a horizontal rectilinear bar (24) which lies at a lower level than that of the lower edge of the said first member (14) so that it lies within the said layer of product defined in the said zone (13); said layer leaving the said zone (13) having impressions left by the dispensers of the said unit (3), so that when the said layer encounters the said second member (15) the product (2) is thereby subjected to a mixing which causes the impressions to disappear and which homogenizes the said product (2) to pulverize possible lumps which may be formed as a result of the pressure on the said product (2) by the dispenser unit (3).

8. A machine according to claim 7,
wherein said bar (24) has a longitudinal axis extending radially with respect to the said central part (23) of the said container (4), a first end close to the said central part (23) and a second end close to the said side wall (12) immediately downstream of the said outlet opening of the said channel (22).

9. A machine according to claim 8,
wherein said third member (16) comprises a vertical wall which extends longitudinally along a parabolic curve which is concave towards the said zone (13), said vertical wall extending from a point close to the said side wall (12) immediately downstream of the said outlet opening of the said channel (22) and terminating close to the said central part (23) to define therewith the said passage (26).

10. A machine according to claim 9,
wherein the side of the said third member (16) close to the said side wall (12) brushes against said side wall to prevent flow of the said product (2) in excess of the said layer other than through the said passage (26).

11. A machine according to claim 1,
wherein said container (4) is a rotating container and the said members (14, 15 and 16) are fixed.

12. A machine according to claim 1,
wherein the said product (2) has a predetermined hygroscopic property as a result of which, during the said relative rotation, aggregation between parts of the said product (2) occurs so as to create a plurality of pellets, said machine further comprising a second device (52) installed in the said container (4) upstream of the said first member (14) and operable to form the said pellets uniformly into a predetermined diameter.

13. A machine according to claim 12, wherein said second device (52) includes a first horizontal shaft (55) and a plurality of disc blades (57) carried uniformly on the said first shaft (55) with a distance between adjacent said blades (57) determining the said diameter of the said pellets and the distance between the said blades (57) and the said bottom wall being close to the distance between the said adjacent blades (57).

14. A machine according to claim 13, wherein a first one of the said blades (57) is close to the said side wall (12) and a last one of the said blades (57) is close to the said passage (26).

15. A machine according to claim 14, wherein longitudinal axis of the said first shaft (550 extends radially of the said container (4).

16. A machine according to claim 15, wherein said blades (57) are mounted freely rotatably on the said shaft (55).

17. A machine according to claim 15, wherein said blades (57) are fixed on said first shaft (55), said first shaft being rotatable.

18. A machine according to claim 17, further comprises a third device (58) operable to scrape thereto.

19. A machine according to claim 12, comprising a fourth device (53) installed between the said first portion (18) and the said zone (13) and operable to compress the pellets slightly to impart a substantially ovoid form thereto.

20. A machine according to claim 19, wherein said fourth device (53) includes a cylindrical roller (61) carried by a second horizontal shaft (62) which is, rotatable; the distance defined between the said roller (61) and the said bottom wall (11) being slightly less than that defined between the said first member (14) and the said bottom wall (11).

21. A machine according to claim 20, wherein the longitudinal axis of the said roller (61) extends radially of the said container (4); the said roller (61) having a length slightly less than the distance between the said central part (23) and the said side wall (12).

22. A machine according to claim 12, further comprising a fifth device (54) installed downstream of the said third member (16) and operable to supply to the said container (4) predetermined quantities of additives which determine the hygroscopic property of the said product (2).

23. A machine according to claim 11, comprising a fixed plate supporting said members (14, 15 and 16).

* * * * *